United States Patent
Elliott

[11] Patent Number: 5,908,404
[45] Date of Patent: Jun. 1, 1999

[54] METHODS FOR INSERTING AN IMPLANT

[76] Inventor: James B. Elliott, 2108 Paso Verde Dr., Hacienda Heights, Calif. 91745

[21] Appl. No.: 09/034,533

[22] Filed: Mar. 3, 1998

Related U.S. Application Data

[63] Continuation of application No. 08/645,101, May 13, 1996, Pat. No. 5,827,293.

[51] Int. Cl.$^6$ .................................................. A61M 31/00
[52] U.S. Cl. ............................ 604/51; 606/107; 604/57; 604/104
[58] Field of Search .............................. 606/107; 604/57, 604/104, 59, 60, 63, 311, 14, 15, 51

[56] References Cited

U.S. PATENT DOCUMENTS

| | | | |
|---|---|---|---|
| 2,513,014 | 6/1950 | Fields | 128/217 |
| 3,744,493 | 7/1973 | Booher et al. | 128/217 |
| 4,086,914 | 5/1978 | Moore | 128/1.2 |
| 4,601,699 | 7/1986 | Crain | 604/64 |
| 4,657,421 | 4/1987 | Lin | 401/57 |
| 4,661,098 | 4/1987 | Bekkering et al. | 604/135 |
| 4,685,904 | 8/1987 | Krebs | 604/164 |
| 4,863,439 | 9/1989 | Sanderson | 604/264 |
| 4,966,478 | 10/1990 | Kuo | 401/57 |
| 4,994,028 | 2/1991 | Leonard et al. | 604/60 |
| 5,019,053 | 5/1991 | Hoffman et al. | 604/220 |
| 5,120,316 | 6/1992 | Morales et al. | 604/148 |
| 5,123,905 | 6/1992 | Kelman | 604/15 X |
| 5,273,532 | 12/1993 | Niezink et al. | 604/62 |

*Primary Examiner*—Wynn Wood Coggins
*Assistant Examiner*—N. Kent Gring
*Attorney, Agent, or Firm*—Christie, Parker & Hale, LLP

[57] ABSTRACT

A method for inserting an implant into a patient utilizing an apparatus comprising a cartridge having a body with a central bore. The body comprises at its proximal end a retention shoulder or hub adapted for retention by an insertion tool. The body further comprises a closure plug received in the proximal end of the bore that seals the bore and that has an exposed surface to engage a plunger rod from an insertion tool. The body further comprises a sealed distal tip of decreasing diameter from the outer surface of the body that terminates in a point adapted for penetrating a pre-existing body orifice or for piercing tissue during insertion into a patient. The tip is frangible into a plurality of segments under pressure exerted by the distal end of the implant, allowing the implant to emerge from the cartridge.

14 Claims, 5 Drawing Sheets

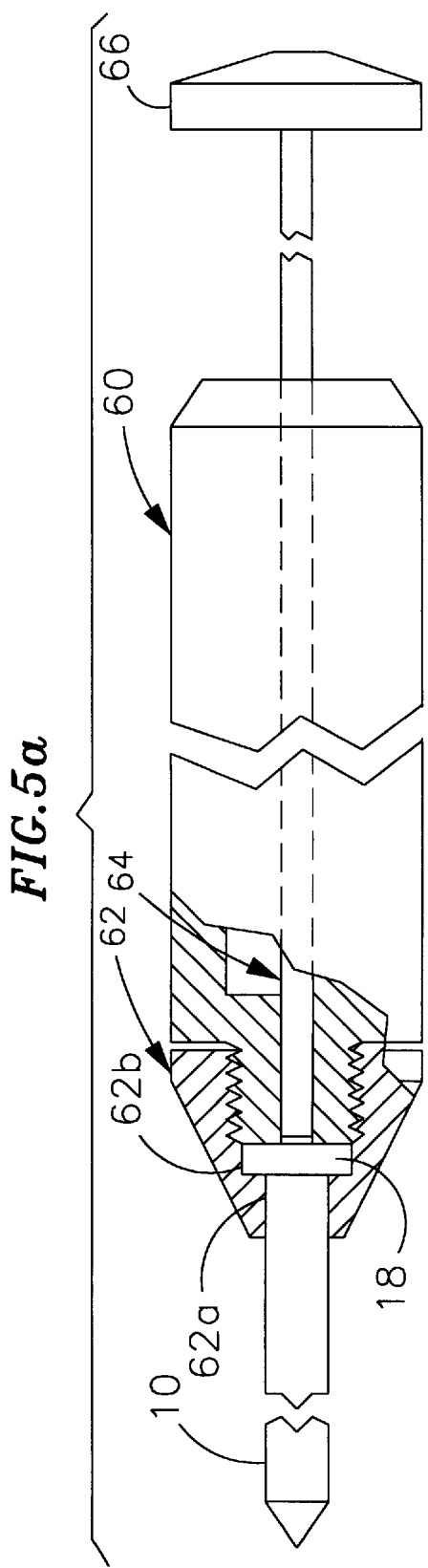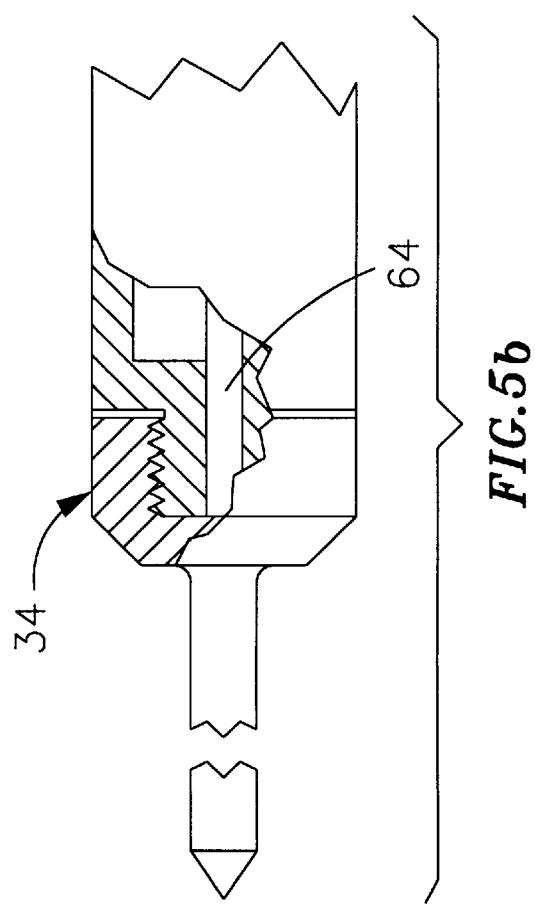

METHODS FOR INSERTING AN IMPLANT

This application is a continuation of application Ser. No. 08/645,101, filed May 13, 1996, now U.S. Pat. No. 5,827,293.

BACKGROUND OF THE INVENTION

1. Field of the Invention

The present invention relates generally to the field of implanting of inert or active medical devices for remedial benefit or for extended release of various drugs. More particularly, the present invention provides a self-contained disposable cartridge having an integral penetration tip which is frangible subsequent to insertion for implanting of a medicament or device maintained in a sterile environment within the sealed cartridge prior to insertion.

2. Description of the Prior Art

Application of medicaments to patients over an extended period of time has become possible with the use of timed release implants (TRI) which are inserted subcutaneously in the patient and provide release of the medicament included in the implant over a significant period of time. Use of TRIs in the contraceptive field and for administration of insulin and other drugs for control of diabetes are becoming conventionally accepted means for medication of patients. Modern genetic engineering is increasingly leading to cures of a variety of diseases by replacement of missing body chemistry. The TRI provides a convenient, medically efficient and cost-effective method of introducing such drugs to a patient.

TRIs and similar devices are currently implanted surgically or using insertion devices having large-bore needles through which the encapsulated implant is inserted. Such devices typically require high-cost sterilizable components due to the size of the implants themselves. Use of a large-bore needle of the type necessary to pass an implant device can cause serious trauma through coring where the hollow needle actually cuts out a plug of tissue when inserted. In order to prevent coring, the use of a stylette or other means to block the needle bore during insertion is required which adds to the complexity of the insertion device, its associated cost and sterilization requirements. Additionally, a determination of the depth of insertion for the implant site and accurate placement of the implant are required. Conventional beveled needles, particularly of large bore, have a tendency to slice through tissue at an angle to the needle axis, thereby making control of needle insertion and consequent accuracy of placement of the implant device, difficult. Alternatively, placement of implant devices is accomplished at surgically accessed sites by manipulation with forceps or other common surgical tools. These procedures take considerable time to perform, result in greater trauma to the patient and require extreme care in avoiding contamination of the implant device during extraction from packaging and handling.

A determination of the depth of the implant typically requires a special gauge, or is measured by approximating the depth of insertion through measurement of the exposed portion of the needle. Either process is typically time-consuming and subject to error or accidental contamination of the implantation site.

It is therefore desirable that an implant insertion device comprise a disposable portion which maintains the implant in a sterile environment and is itself easy to maintain in a sterile condition prior to use. It is further desirable that the implant device include a symmetrical non-coring piercing device with integrated insertion depth measurement to allow accurate insertion of an implant through an existing orifice, subdurally, subcutaneously or in an intramuscular location as appropriate for the particular implant or device.

SUMMARY OF THE INVENTION

The present invention overcomes the shortcomings of the prior art by providing an integral cartridge assembly for an implant which incorporates a body having an internal bore for sterile containment of the implant device, the body terminating at a proximal end in a retention shoulder suitable for manually gripping the cartridge, and adapted for securing the cartridge in an insertion tool. The cartridge body terminates at the distal end in a symmetrical piercing tip which is scored to produce frangible segments. A closure plug inserted in the bore at the proximal end of the cartridge seals the implant within the body of the cartridge, maintaining a sterile environment, and provides a piston for engagement of the implant device to urge the implant against the distal tip subsequent to insertion of the tip into the patient, fracturing the tip along the scoring to emerge from the cartridge. Striations or grooves on the exterior of the cartridge body at predetermined locations define the insertion depth for the cartridge, allowing an immediate determination of proper insertion of the implant device. Integral reinforcement of the attachment zone of the frangible segments of the tip to the cartridge body precludes loss of the frangible segments during removal of the cartridge from the patient and the entire cartridge is disposable, thereby precluding repeated sterilization of a complex surgical instrument for reuse.

The cartridge is sterilized by standard autoclave or radiation processes and sterility is maintained prior to use for inserting an implant device into a patient using standard biobarrier packaging, commonly available in the health care and medical industries, for protecting sterile integrity of medical devices.

BRIEF DESCRIPTION OF THE DRAWINGS

FIG. 1b is a forward end view of the distal tip of the embodiment shown in FIG. 1a;

FIG. 1c is a section view along line CC of FIG. 1a;

FIG. 2a is a partial section side view of a cartridge incorporating a second embodiment of the invention;

FIG. 2b is a front-end view of the distal view of the tip of the cartridge shown in FIG. 2a;

FIG. 2c is a sectional view along line CC of FIG. 2a;

FIG. 2d is a detailed view showing assist plug for fracturing of the distal tip;

FIG. 3b is a front-end view of the distal tip of the cartridge shown in FIG. 3a;

FIG. 3c is a sectional view along CC of FIG. 3a;

FIG. 5a is a partial sectional side view of an insertion apparatus for cartridges incorporating the present invention; and FIG. 5b is a partial view of a second embodiment of the insertion apparatus of FIG. 5a employing an alternative means for attachment of the cartridge.

DETAILED DESCRIPTION

Figure 1A:
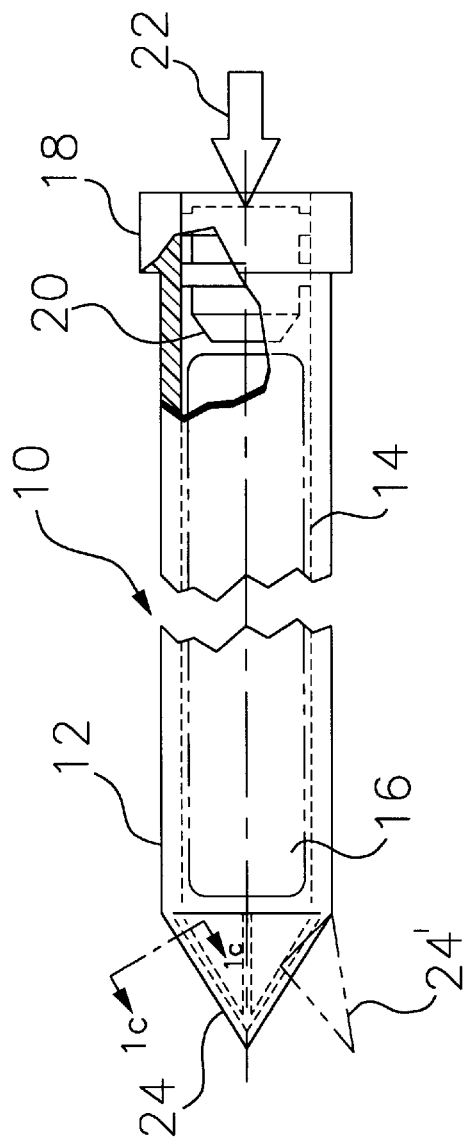
FIG. 1a is a partially sectioned side view of a cartridge incorporating the present invention.
Figure 1B:
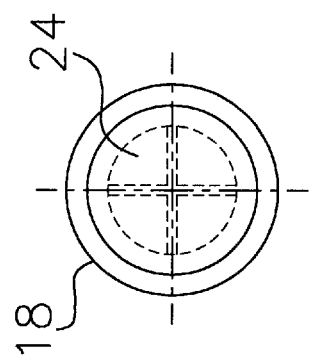
Figure 1C:
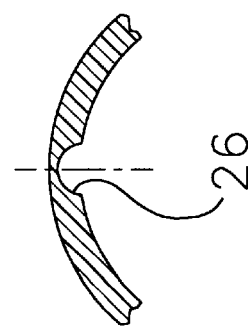

FIGS. 1a, 1b and 1c disclose a first embodiment of the invention employing a cartridge 10 which has a substantially cylindrical body 12 with an internal bore 14. One or more implant devices 16 are contained within the bore.

At a proximal end, the body of the cartridge terminates in a retention shoulder 18. The retention shoulder extends from the cylindrical body of the cartridge to allow a convenient handling site for the medical technician or doctor, and is further adapted to retain the cartridge in the insertion apparatus to be described in greater detail subsequently. A closure plug 20 is received in the opening of the bore at the proximal end of the body to seal the bore, thereby maintaining a sterile environment for the implant device. The closure plug also acts as a piston engaged by a rod in the insertion device, to be described in greater detail subsequently, which exerts a force in the direction of arrow 22, urging the plug against the implant device.

The distal end of the cartridge body terminates in a pointed tip 24 having four frangible segments, for the embodiment best seen in FIG. 1b, which are defined by circular cross section grooves 26 internal to the tip, best seen in FIG. 1c. The grooves define high-stress fracture lines in the tip. Urging of the implant device against the interior of the tip, by the plug and rod of the insertion device, causes the tip to fracture along the grooves into the frangible segments shown in phantom in FIG. 1a denominated 24' allowing the implant device to emerge from the cartridge.

The pointed tip of the cartridge allows penetration of epidural tissue to the appropriate depth for extrusion of the implant device. The grooves forming the high-stress fracture lines are imparted to the tip through scoring or machining of the interior of the tip subsequent to molding or by appropriately placed splines on the molding mandrel for the cartridge.

The embodiments of the invention shown in the drawings are molded and/or machined from surgical purity plastic polymers. Standard injection molding processes for medical components are well known in the art and will not be described in detail herein.

Figures 2A, 2B, 2C, 2D:
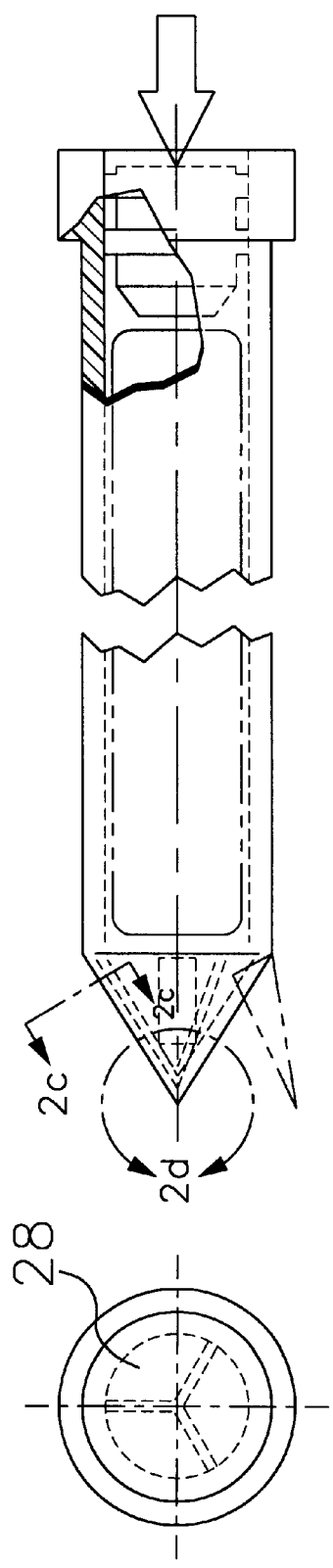

FIGS. 2a, 2b, 2c and 2d show a second embodiment of the present invention having a general configuration and function similar to that disclosed for FIGS. 1a–c. The second embodiment incorporates a tip having three frangible segments 28 as best seen in FIG. 2b defined by V-shaped grooves 30, best seen in FIG. 2c, which are internal to the tip. Additionally, as disclosed in FIG. 2d, the second embodiment of the invention employs an assist plug 32 having a smaller diameter than the implant device. The assist plug is inserted into the cartridge prior to the implant device, and contacts the implant device on a first end, and the interior of the tip on a second end. The reduced diameter of the assist plug bears on a smaller relative area of the tip, thereby increasing the stress by amplifying the external pressure by concentrating force from the implant for initial fracture of the frangible segments of the tip, thereby enhancing expulsion of the implant device. The assist plug, in the embodiment shown in the drawings, is made of the same material as the implant device, or a harmless bioresorbable material such as suture-grade collagen, polylactic polymer, or polyglycolic polymer. Shaping of the plug to achieve maximum stress on the tip through force applied to the plug by the implant device is desirable.

Figure 3A:
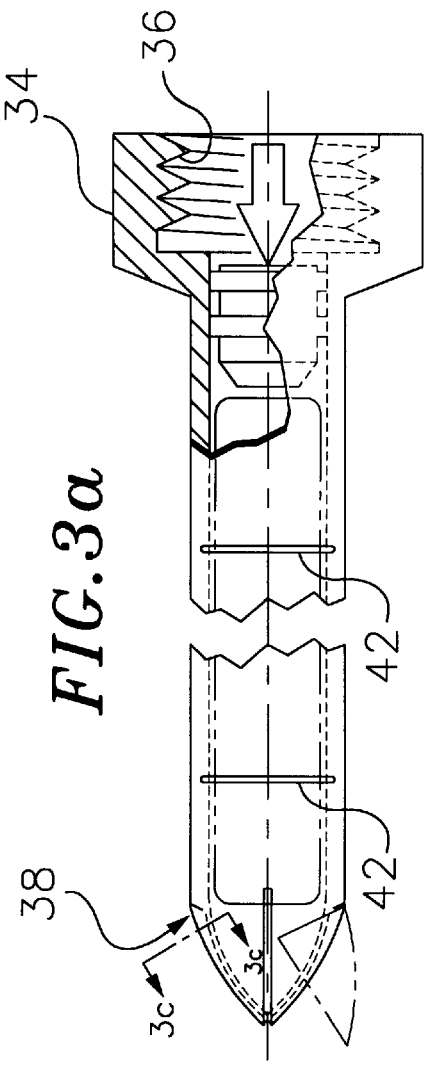
FIG. 3a is a partial section side view of a cartridge incorporating a third embodiment of the invention.
Figure 3C:
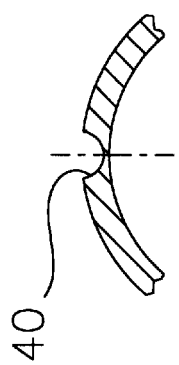
Figure 3B:
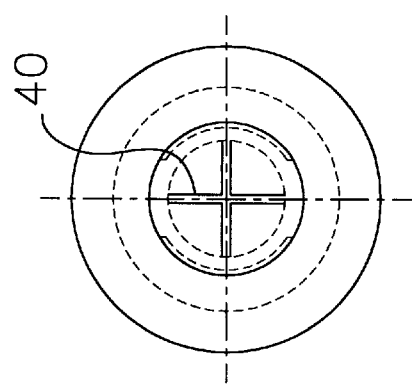

FIGS. 3a, 3b and 3c demonstrate a third embodiment of the invention. In the third embodiment of the invention the termination of the cartridge body at the proximal end incorporates a retention hub 34 having internal threads 36 for attachment of the cartridge to the insertion device. The retention hub is advantageous over the retention shoulder of the first two embodiments in applications wherein sizing of the overall cartridge is small and greater grasping area on the cartridge is necessary for use by the technician in attaching the cartridge to the insertion device. The third embodiment of the invention also employs a tip 38 having a curved profile, best seen in FIG. 3a, and external circular cross section grooves 40, best seen in FIGS. 3b and 3c, for creating the fracture lines for the frangible segments of the tip. Shaping of the exterior grooves is also advantageous in assisting in separation of epidural tissues during insertion of the tip and cartridge to a proper depth for the implant device.

The body of the cartridge incorporates striations 42 on the exterior surface of the cartridge body. The striations are placed at predetermined locations along the cartridge body to provide a visual cue for depth of penetration of the tip for appropriate placement of the implant device. Shallow grooves or other means providing visible yet biocompatible markings are appropriate for the striations.

Figure 3D:
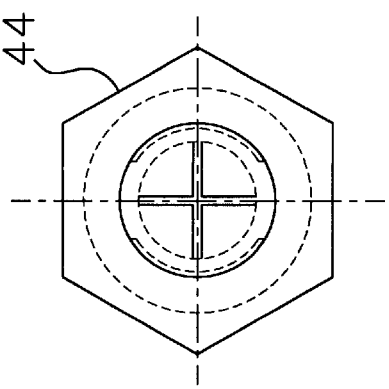
FIG. 3d is an end view showing an alternate embodiment of the retention hub for the cartridge shown in FIGS. 3a and 3b.

FIG. 3d shows an alternate configuration for the retention hub of the third embodiment which incorporates hexagonal flats 44 to assist in tightening the threaded connection of the retention hub to the insertion tool using fingers or a wrench.

Figure 4C:
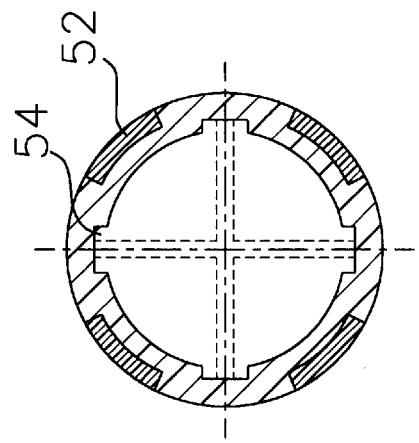
FIG. 4c is a sectional view showing a third embodiment for external reinforcing members for the frangible tip segments.

To assure that the frangible segments of the distal tip do not create loose debris when fractured during expulsion of the implant device, reinforcing of the attachment edge of the frangible segments to the cartridge body is employed. FIGS. 4a, 4b, 4c and 4d demonstrate alternative embodiments for such reinforcement. FIG. 4a demonstrates the use of embedded reinforcement members 46 integrally molded into the cartridge and extending into the frangible tip segments and body to reinforce the unfractured interface between the tip segment and body.

Figure 4B:
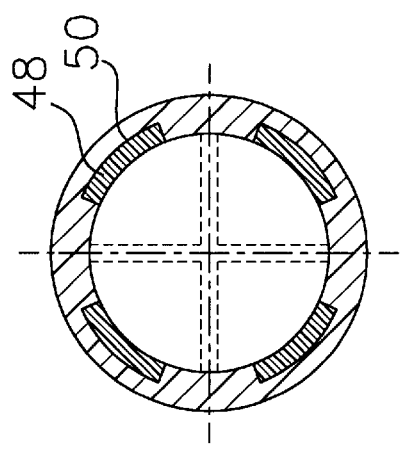
FIG. 4b is a sectional view showing a second embodiment for internal reinforcing members for the frangible tip segments.

FIG. 4b demonstrates a second approach employing internal reinforcing members 48 which constitute strips of reinforcement material embedded in internal grooves 50 extending into the tip and body of the cartridge. Bonding of segments of reinforcement strips into premolded grooves, or integral molding of the cartridge over an insert, preformed from metal or polymer having high ductility and flexibility, placed on the molding mandrel, are employed for fabrication.

Figure 4D:
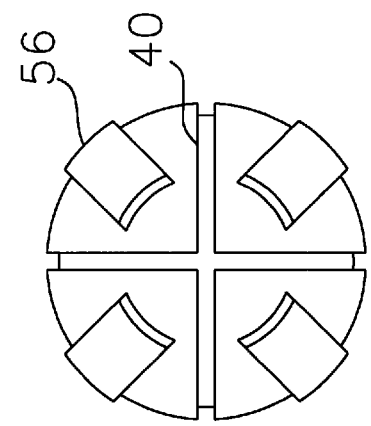
FIG. 4d is a front view showing a fourth embodiment for external reinforcing members for the frangible tip segments.
Figure 4A:
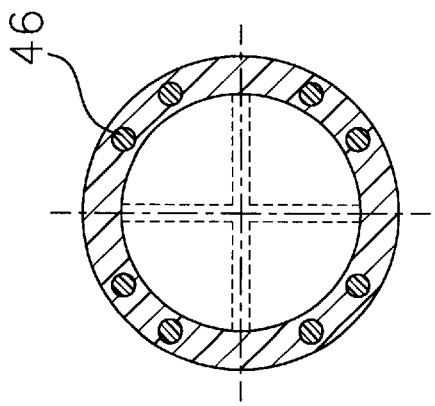
FIG. 4a is a sectional view showing embedded reinforcement members for the frangible tip segments of the cartridge.

FIG. 4c demonstrates an alternative embodiment for reinforcement employing external reinforcing members 52 in grooves extending on the exterior surface of the frangible tip segments and cartridge body. As with the internal reinforcing members, the external reinforcing members are bonded in premolded grooves in the cartridge or integrally molded into the cartridge by preplacement in the mold cavity. Alternatively, Mylar tape strips 56 or similar material are applied by adhesive or other bonding mechanism to the cartridge after molding in the premolded grooves or, with sufficiently thin material, directly to the exterior surface of the tip as shown in FIG. 4d.

In each of the embodiments for reinforcement previously described, the reinforcing members act as a hinge for the frangible tip segments, circumferential scoring or grooves 54 intermediate the reinforcing members to enhance fracture of the frangible tip segments, are employed in alternative designs to assure integrity of the reinforcing member hinges during fracture of the tip.

The configuration of the present invention is particularly suited for packaging in standard sterilizable blister pack or similar forms having an access tab end adjacent the proximal end of the cartridge. Handling of the cartridge is accomplished using the retention shoulder, thereby avoiding finger contamination of the remainder of the cartridge during attachment to the insertion tool.

Loading of the implant in the cartridge is accomplished in a standard clean room environment which may be automated based on the configuration of the embodiments of the invention disclosed in the drawings with installation of the implant and assist plug, when employed, followed by closure of the cartridge with the closure plug. Radiation sterilization of the cartridge before or after packaging using standard FDA practice recommendations is easily accomplished.

The insertion tool employed with the cartridge incorporating the present invention includes a cartridge attachment portion comprising a retainer groove and ring assembly receiving the retention shoulder of the embodiments shown in FIGS. 1a and 2a of the drawings, or alternatively, a threaded tip for insertion in the retention hub of the embodiment of the invention shown in FIG. 3a. For the embodiment shown in the drawings, a plunger assembly having a rod centrally positioned in the insertion tool for engagement of the exposed end of the closure plug in the cartridge is employed with a flat to be engaged by the thumb while a barrel or handle of the insertion tool is grasped in the fingers and palm of the hand. This embodiment of the insertion tool is also usable by grasping the barrel with one hand while using a finger or thumb of the other hand to depress the plunger. Alternatives providing mechanical advantage through ratchet or spring loaded actuators including travel limitation devices for the rod to assure proper dispensing of the implant while maintaining the closure plug within the cartridge body for removal with the cartridge from the patient are employed in tools for application in which consecutive multiple insertions are anticipated.

An insertion tool for the cartridge of the present invention is shown in FIG. 5a. The insertion tool comprises a handle 60 which incorporates an attachment nut 62. The attachment nut includes a cylindrical aperture through which the body of the cartridge is received and an offset 62b which receives and retains the retention shoulder on the cartridge. In the embodiment shown in the drawings, the attachment nut incorporates an internal thread, mating to a threaded nipple on the handle. A plunger rod 64 extending through the handle is aligned with the proximal end of the cartridge to engage the plug 20. An alternative embodiment (not shown) with standard finger grips and thumb ring for depressing of the plunger/rod assembly is employed for enhanced one handed manipulation in surgical placement of implants.

Sterility of the insertion tool is enhanced through the use of a prophylactic covering, either preattached to the cartridge assembly or separably mountable in a form such as that disclosed in U.S. Pat. No. 5,228,851 to Burton. While the Burton device is disclosed with regard to dental tools, application to an insertion apparatus as disclosed herein would reduce any requirements for sterilizing the insertion tool employed with the present invention.

To employ the cartridge for insertion of an implant, the physician or technician removes the cartridge from its packaging by grasping the retention shoulder, thereby maintaining the sterile condition of the tip and body of the cartridge. The cartridge is inserted through the aperture of the attachment nut and the attachment nut is threadably engaged to the handle of the insertion tool. After preparation of the implant placement site with local anesthetic and other procedures as necessary, the physician or technician uses the handle of the insertion tool to pierce the tissue of the patient with the cartridge tip using the markings on the cartridge body to determine proper depth of insertion. Plunger 66 is then depressed to urge the rod against the plug which in turn urges the implant device against the interior of the tip of the cartridge fracturing the frangible tip and allowing the implant device to emerge from the cartridge. The plunger rod is sized to provide contact of the plunger with the handle body upon complete insertion of the implant device or alternatively, is marked to allow visual confirmation of proper depression depth.

The insertion tool and cartridge are alternatively employed to introduce an implant or device into an existing body cavity, vessel or organ through a natural orifice or in conjunction with a surgical procedure.

Upon completion of the insertion of the implant device the physician or technician removes the cartridge from the patient using the handle. The attachment nut is removed from the handle and the cartridge disengaged from the attachment nut and properly discarded. The insertion tool is then reusable with additional implant cartridges. Sterility of the insertion device may be accomplished through the use of latex prophylactic devices as known in the prior art previously described or by standard surgical instrument autoclave or gas sterilization processes.

The insertion tool shown in FIG. 5a is adapted in alternative embodiments for direct external insertion of the cartridge. A slot and interconnecting aperture in a sidewall of the handle receives the cartridge body and retention shoulder. The aperture is sized to receive the shoulder to retain the cartridge and resist longitudinal movement of the cartridge within the insertion tool. A rotating barrel to close the aperture and slot subsequent to insertion of the cartridge may also be employed.

FIG. 5b discloses a second embodiment for the insertion tool employed with the alternative embodiment for the insertion cartridge shown in FIG. 3a which employs a retention hub 34 having internal mating threads. The retention hub on the cartridge eliminates the necessity for the separate attachment nut and provides direct attachment of the cartridge to the insertion tool handle with alignment of the plunger rod 64 for engagement of the plug.

Operation of the alternative insertion tool is substantially identical to that described for the insertion tool disclosed in FIG. 5a.

Those skilled in the art will recognize alternative approaches for urging the plunger rod through the insertion tool to engage the cartridge plug including spring loaded actuation arrangements such as that found in mechanical pencils which are particularly suited for insertion of multiple implants from a single cartridge.

Having now described the invention in detail as required by the patent statutes, those skilled in the art will recognize modifications and substitutions to the embodiments disclosed in this specification. Such modifications and substitutions are within the scope and intent of the present invention as defined in the following claims.

What is claimed is:

1. A method for inserting an implant in a patient, comprising:

(a) providing an apparatus comprising a cartridge having an internal surface and an external surface and comprising:
   a body with a central bore, a proximal and distal end, an implant contained within the central bore,
   a closure plug sealing the proximal end of the bore, and
   a distal tip of decreasing diameter from the outer surface of the body, on said distal end the distal tip having an inside and an outside and terminating in a point adapted for piercing the tissue of the patient, said tip being frangible into a plurality of segments under pressure from a distal end of the implant;

(b) inserting the tip of the apparatus into the tissue of the patient;

(c) urging the plug against the implant to urge the implant against the inside of the distal tip, thereby fracturing the distal tip and allowing the implant to emerge from the cartridge.

2. A method according to claim 1, wherein the apparatus further comprises an assist plug in the cartridge between the implant and the distal tip, whereby urging of the plug against the implant urges the implant against the assist plug and the assist plug against the distal tip, thereby fracturing the distal tip.

3. A method according to claim 1, wherein the plug is urged against the implant by an insertion tool attached to the cartridge.

4. A method according to claim 3, wherein the insertion tool is removable from the cartridge.

5. A method according to claim 4, wherein the cartridge further comprises a means for attaching the insertion tool to the cartridge.

6. A method according to claim 5, wherein the attaching means is a retention shoulder extending radially from an outer surface of the body, the retention shoulder being adapted for retention in an insertion tool.

7. A method according to claim 5, wherein the attaching means is a retention hub extending radially from an outer surface of the body, the retention hub incorporating a threaded attachment adapted to be received on a mating thread on the insertion tool.

8. A method according to claim 1, wherein the implant is a sterile implant.

9. A method according to claim 1, further comprising sterilizing the cartridge prior to the implant being inserted into the patient.

10. A method according to claim 1, wherein the distal tip comprises a plurality of grooves on a surface of the distal tip, the grooves extending substantially from the body of the cartridge to the pointed end of the distal tip.

11. A method according to claim 10, wherein the grooves are on the internal surface of the distal tip.

12. A method according to claim 10, wherein the grooves are on the external surface of the distal tip.

13. A method according to claim 1, wherein the apparatus further comprises reinforcement means extending from the cartridge body to the frangible segments of the distal tip capable of preventing separation of the segments subsequent to fracture of the tip.

14. A method according to claim 1, wherein the cartridge incorporates visible markings on its external surface to allow a determination of the depth of penetration of the distal tip.

* * * * *